US010159797B2

United States Patent
Andersen et al.

(10) Patent No.: US 10,159,797 B2
(45) Date of Patent: *Dec. 25, 2018

(54) LOGGING DEVICE FOR DRUG DELIVERY DEVICE

(71) Applicant: Novo Nordisk A/S, Bagsvaerd (DK)

(72) Inventors: Jens Christian Andersen, Roskilde (DK); Nikolaj Frogner Krusell, Copenhagen OE (DK); Preben Mikael Nielsen, Holbaek (DK)

(73) Assignee: Novo Nordisk A/S, Bagsvaerd (DK)

(*) Notice: Subject to any disclaimer, the term of this patent is extended or adjusted under 35 U.S.C. 154(b) by 0 days.
This patent is subject to a terminal disclaimer.

(21) Appl. No.: 15/315,414

(22) PCT Filed: Jun. 4, 2015

(86) PCT No.: PCT/EP2015/062499
§ 371 (c)(1),
(2) Date: Dec. 1, 2016

(87) PCT Pub. No.: WO2015/185687
PCT Pub. Date: Dec. 10, 2015

(65) Prior Publication Data
US 2017/0182256 A1 Jun. 29, 2017

(30) Foreign Application Priority Data
Jun. 6, 2014 (EP) .................... 14171456

(51) Int. Cl.
A61M 5/315 (2006.01)
A61M 5/20 (2006.01)
(Continued)

(52) U.S. Cl.
CPC .......... *A61M 5/31546* (2013.01); *A61M 5/20* (2013.01); *A61M 5/24* (2013.01);
(Continued)

(58) Field of Classification Search
CPC .. A61M 5/31546; A61M 5/3202; A61M 5/24; A61M 2205/583; A61M 2205/50;
(Continued)

(56) References Cited

U.S. PATENT DOCUMENTS 5,820,602 A 10/1998 Kovelman et al.
6,248,090 B1 6/2001 Jensen et al.
(Continued)

FOREIGN PATENT DOCUMENTS

EP 2060284 A1 5/2009
EP 2062606 A1 5/2009
(Continued)

*Primary Examiner* — Amber Stiles
(74) *Attorney, Agent, or Firm* — Wesley Nicholas

(57) ABSTRACT

An add-on logging device (100, 300) mounted to a drug delivery device is turned on when the cap is removed. After a given amount of time in inactivity the sensor means of the add-on device is turned off automatically to save energy. If the user takes a dose of drug this is not detected as the add-on device is only turned on when the cap is removed. According to the present invention a warning message is provided when the cap is re-mounted after the sensor means has been turned off automatically, the warning message indicating to a user that an expelled dose may not have been detected.

14 Claims, 4 Drawing Sheets

(51) Int. Cl.
*A61M 5/24* (2006.01)
*G06F 19/00* (2018.01)
*A61M 5/32* (2006.01)
*A61M 5/31* (2006.01)

(52) U.S. Cl.
CPC .... *A61M 5/31545* (2013.01); *A61M 5/31565* (2013.01); *A61M 5/3202* (2013.01); *G06F 19/00* (2013.01); *G06F 19/3468* (2013.01); *A61M 2005/2407* (2013.01); *A61M 2005/3125* (2013.01); *A61M 2005/3126* (2013.01); *A61M 2205/14* (2013.01); *A61M 2205/18* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/581* (2013.01); *A61M 2205/583* (2013.01); *A61M 2205/6072* (2013.01); *A61M 2205/6081* (2013.01); *A61M 2205/8212* (2013.01)

(58) Field of Classification Search
CPC ........ A61M 2205/52; A61M 2205/502; A61M 2005/3126; A61M 2205/18; A61M 2205/581; A61M 2205/8212; A61M 2205/14; A61M 2205/3592; A61M 2205/3584; A61M 2005/2407; G06F 19/3468
See application file for complete search history.

(56) References Cited

U.S. PATENT DOCUMENTS

| | | |
|---|---|---|
| 8,221,385 B2 | 7/2012 | Estes |
| 2004/0062148 A1* | 4/2004 | Skyggebjerg ......... A61M 5/178 368/107 |
| 2009/0318865 A1 | 12/2009 | Moller et al. |
| 2013/0245545 A1 | 9/2013 | Arnold et al. |
| 2017/0182256 A1 | 6/2017 | Andersen et al. |
| 2017/0209650 A1* | 7/2017 | Andersen ............ G06F 19/3468 |

FOREIGN PATENT DOCUMENTS

| | | |
|---|---|---|
| EP | 2294975 A1 | 3/2011 |
| WO | 0126710 | 4/2001 |
| WO | 9733638 | 9/2003 |
| WO | 2004010231 A2 | 1/2004 |
| WO | 2006069455 A1 | 7/2006 |
| WO | 2007107564 A1 | 9/2007 |
| WO | 2008091838 A2 | 7/2008 |
| WO | 2010037828 A1 | 4/2010 |
| WO | 2010052275 A2 | 5/2010 |
| WO | 2010098927 A1 | 9/2010 |
| WO | 2010128493 A2 | 11/2010 |
| WO | 2013004844 A1 | 1/2013 |
| WO | 2013050535 A2 | 4/2013 |
| WO | 2014161953 A1 | 10/2014 |

* cited by examiner

LOGGING DEVICE FOR DRUG DELIVERY DEVICE

CROSS-REFERENCE TO RELATED APPLICATIONS

This application is a 35 U.S.C. § 371 National Stage application of International Application PCT/EP2015/062499 (published as WO 2015/185687), filed Jun. 4, 2015, which claims priority to European Patent Application 14171456.8, filed Jun. 6, 2014; the contents of which are incorporated herein by reference.

The present invention generally relates to medical devices for which the generation, collecting and storing of data are relevant. In specific embodiments the invention relates to devices and systems for capturing and organizing drug delivery dose data in an efficient and user-friendly way.

BACKGROUND OF THE INVENTION

In the disclosure of the present invention reference is mostly made to drug delivery devices used e.g. in the treatment of diabetes by delivery of insulin, however, this is only an exemplary use of the present invention.

Drug injection devices have greatly improved the lives of patients who must self-administer drugs and biological agents. Drug injection devices may take many forms, including simple disposable devices that are little more than an ampoule with an injection means or they may be durable devices adapted to be used with pre-filled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from which the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of ejection information from medication delivery systems based on the assumption that ejected doses corresponds to injected doses.

Though some injection devices integrate this monitoring/acquisition mechanism into the device itself, e.g. as disclosed in US 2009/0318865 and WO 2010/052275, most devices of today are without it. The most widely used devices are purely mechanical devices either durable or prefilled. The latter devices are to be discarded after being emptied and so inexpensive that it is not cost-effective to build-in electronic data acquisition functionality in the device itself. Addressing this problem a number of solutions have been proposed which would help a user to generate, collect and distribute data indicative of the use of a given medical device.

For example, WO 2007/107564 describes an electronic "add-on" module adapted to be attached to and measure signals generated by a standard mechanical pen device, the module relying on e.g. the sounds inherently produced by such a device during operation. WO 2010/037828 discloses a further add-on module adapted to be mounted on a pen device and create a time log for data representing sizes of doses expelled by the drug expelling mechanism of the pen device.

Alternatively, in order to provide pre-filled drug delivery devices which more reliably allow detection of an out-dosed amount of drug, it has been proposed to modify such pre-filled drug delivery devices to provide them with structures making them more suitable for cooperation with external detection means, thereby providing more reliable and accurate determination of out-dosed drug amounts. For example, PCT/EP2012/069729 discloses a drug delivery device in which a rotating piston rod is provided with a magnet allowing an add-on logging module to detect the axial position of the magnet by means of 3D magnetometers.

Having regard to the above, it is an object of the present invention to provide systems, devices and methods allowing capturing and organizing drug delivery dose data in an efficient and user-friendly way.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a general aspect of the invention a logging device is provided, the logging device being adapted to be releasably attached to a drug delivery device or being formed integrally therewith (i.e. not to be detached by a user), the drug delivery device comprising a drug reservoir or means for receiving a drug reservoir, the drug reservoir comprising an outlet portion, a detachable cap adapted to cover the drug reservoir outlet portion in a mounted position, and drug expelling means comprising dose setting means allowing a user to set a dose amount of drug to be expelled. The logging device further comprises electronic circuitry comprising sensor means adapted to capture a property value related to a dose amount of drug expelled from a reservoir by the expelling means during an expelling event when the logging device has been attached to a drug delivery device, processor means adapted to determine dose amounts based on captured property values, memory means adapted to store at least one dose amount, display means adapted to display (i) a determined dose amount and/or a time value, and (ii) a warning message, and switch means adapted to be operated, when the logging device has been attached to a drug delivery device or is formed integrally therewith, between an off-state when the cap is in the mounted position and an on-state when the cap has been detached. A given dose amount may be stored in the memory in the form of e.g. the "native" detected property representing an amount of drug or as a calculated amount of drug. In such a device the sensor means is turned on when the switch is operated from the off- to the on-state, the sensor means is turned off when the switch is operated from the on- to the off-state, the sensor means is turned off automatically when a predetermined amount of time has lapsed, and the display means is turned on to display a warning message when the switch is operated from the on- to the off-state and the sensor means has been turned off automatically, the warning message indicating to a user that an expelled dose may not have been captured.

Correspondingly, in a first specific aspect of the invention a logging device adapted to be releasably attached to a drug delivery device is provided, the drug delivery device comprising a drug reservoir or means for receiving a drug reservoir, the drug reservoir comprising an outlet portion, a detachable cap adapted to cover the drug reservoir outlet portion in a mounted position, drug expelling means comprising dose setting means allowing a user to set a dose amount of drug to be expelled, and electronic circuitry adapted to create a log of expelled dose amounts of drug. The electronic circuitry comprises sensor means adapted to capture a property value related to a dose amount of drug expelled from a reservoir by the expelling means during an expelling event when the logging device has been attached to a drug delivery device, processor means adapted to determine dose amounts based on captured property values, memory means adapted to store at least one dose amount, display means adapted to display a determined dose amount and/or a time value as well as a warning message, the electronic circuitry further comprising switch means. A time value may be associated with each stored dose amount. With the logging device attached to a drug delivery device the switch means is adapted to be operated between an off-state when the cap is in the mounted position and an on-state when the cap has been detached. In such an arrangement the sensor means is turned on when the switch is operated from the off- to the on-state, the sensor means is turned off when the switch is operated from the on- to the off-state, the sensor means is turned off automatically when a predetermined amount of time has lapsed, and the display means is turned on to display a warning message when the switch is operated from the on- to the off-state and the sensor means has been turned off automatically, the warning message indicating to a user that an expelled dose may not have been captured.

The predetermined amount of time is initially counted from when the cap is removed, however, the counter may be reset when a given event is detected, e.g. a successful logging of an expelled dose of drug, this allowing a user to divide a given dose into split doses without "time constraints".

As appears, an add-on device mounted to a pen device is turned on when the cap is removed, and after a given amount of time in inactivity the add-on device is turned off automatically, this to save energy. However, after this has happened the user may take a dose of drug which is then not detected as the add-on device is only turned on when the cap is removed. By providing a warning message when the cap is re-mounted after the sensor means has been turned off automatically, the warning message indicates to a user that an expelled dose may not have been captured, this allowing the user to take appropriate action if a dose was actually expelled.

When the cap is re-mounted after a "normal" use event, the display means may display a determined dose amount together with a time value. Alternatively, only a dose amount or only a time value may be shown. The time may be a real time value or the time since a given dose amount was stored.

In an exemplary embodiment the display means is turned on for a predetermined amount of time to display a message when the switch is operated from the on- to the off-state, the message being in the form of the last determined dose amount and/or a time value when the display is turned on without the sensor means having been turned off automatically, or the warning message when the display is turned on with the sensor means being turned off automatically. To save energy the sensor means may be turned on with a time delay when the switch is operated from the off- to the on-state, this allowing the user to check the latest log value without turning on the sensor system.

Addressing the situation in which he user desires to split a given (large) dose, stored dose amounts determined within a given time period may be combined to a single combined dose amount. The given time period may be initiated by a detected expelling event taking place a given amount of time after a previous detected expelling event, or after a given detected action.

When two or more dose amounts are determined within a given time period they may be combined automatically, or the user may be prompted to accept that the two or more dose amounts determined within a given time period are combined. Combined amounts may be indicated as such in the display. A determined dose amount below a given value, e.g. below 2 or 3 units of insulin, may be estimated to be a priming or an air shot and thus not combined as a log entry. When a combined dose amount is calculated and stored the individual doses may remain stored and subsequently retrieved when desired. The stored and retrievable data may comprise all determined dose amounts, i.e. including air shots and dose amounts determined in a sensor time-out event but before the sensors were turned off. A time value may be associated with each stored dose amount. For a combined dose e.g. the last time value may be used. The electronic circuitry may comprise transmitter means adapted to transmit stored data to an external receiver, e.g. by means of NFC or Bluetooth.

The sensor means may be adapted to capture a property value in the form of an amount of rotation of a magnetic member arranged in the drug delivery device, the amount of rotation of the magnetic member corresponding to the amount of drug expelled from a reservoir by the expelling means. The electronic circuitry may comprise transmitter means adapted to transmit stored data to an external receiver, e.g. by means of NFC.

The above-described logging device may be provided in combination with a drug delivery device, thereby forming a drug delivery system, the drug delivery device comprising a drug reservoir or means for receiving a drug reservoir, the drug reservoir comprising an outlet portion, a detachable cap adapted to cover the drug reservoir outlet portion in a mounted position, and drug expelling means comprising dose setting means allowing a user to set a dose amount of drug to be expelled, wherein the logging device is releasably attachable to the drug delivery device.

In an exemplary embodiment the drug delivery device further comprises an identifier, e.g. a colour or in the form of a barcode, representing information for the specific drug type contained in the reservoir or the specific drug delivery device, with the logging device further comprising means for capturing information from the identifier, wherein the electronic circuitry is adapted to create a log for a given identifier.

In a further specific aspect of the invention a drug delivery system is provided, comprising a drug reservoir or means for receiving a drug reservoir, the drug reservoir comprising an outlet portion, a detachable cap adapted to cover the drug reservoir outlet portion in a mounted position, drug expelling means comprising dose setting means allowing a user to set a dose amount of drug to be expelled, electronic circuitry comprising sensor means adapted to capture a property value related to the dose amount of drug expelled from the reservoir by the expelling means during an expelling event, processor means adapted to determine dose amounts based on captured property values, memory means adapted to store at least one dose amount, display means adapted to display a determined dose amount and/or a time value, and a warning message, and switch means adapted to be operated between an off-state when the cap is in the mounted position and an on-state when the cap has been detached from the system, wherein the sensor means is turned on when the switch is operated from the off- to the on-state, the sensor means is turned off when the switch is operated from the on- to the off-state, the sensor means is turned off automatically when a predetermined amount of time has lapsed, and the display means is turned on to display a warning message when the switch is operated from the on- to the off-state and the sensor means has been turned off automatically, the warning message indicating to a user that an expelled dose may not have been captured.

The system may be in the form of an integrated drug delivery device comprising the drug reservoir or means for receiving a drug reservoir, the drug expelling means, and the electronic circuitry. The integrated device may be provided with the above-described features of a separate logging device.

In order to capture a property value related to a dose amount of drug expelled a number of technologies could be used. For example, for an integrated arrangement capture could be based on galvanic contacts, optical sensors or magnetic sensors. Indeed, for an external attachable logging device the same principles could be used, however, by using magnetic detection it would be possible to detect movements inside the delivery device without having to provide openings or contacts in the housing wall. For a given expelling mechanism a number of components will normally be moved corresponding to an expelled amount of drug, e.g. a piston rod will move axially and a drive member for moving the piston rod may rotate. Correspondingly, a property value could be either axial displacement or amount of rotation, or a combination of both. For example, if a given component may rotate more than 360 degrees in order to expel a given dose, the amount of rotation may be captured by counting increments or, alternatively, by determining the rotational position of the rotating component and combine it with information relating to the number of full rotations or the axial position of an axially moved component.

In the context of the present application and as used in the specification and the claims, the term processor means covers any combination of electronic circuitry suitable for providing the specified functionality, e.g. processing and storing data as well as controlling all connected input and output devices. A processor will typically comprise one or more CPUs or micro-processors which may be supplemented by additional devices for support, memory or control functions. For example, in case a communication interface is provided (e.g. wireless), the transmitter and receiver may be fully or partly integrated with a processor, or may be provided by individual units. Each of the components making up the processor circuitry may be special purpose or general purpose devices. The term display means covers any type of display capable of visually providing the specified functionality, e.g. a LCD or OLED.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin.

BRIEF DESCRIPTION OF THE DRAWINGS

In the following exemplary embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Figure 1A:
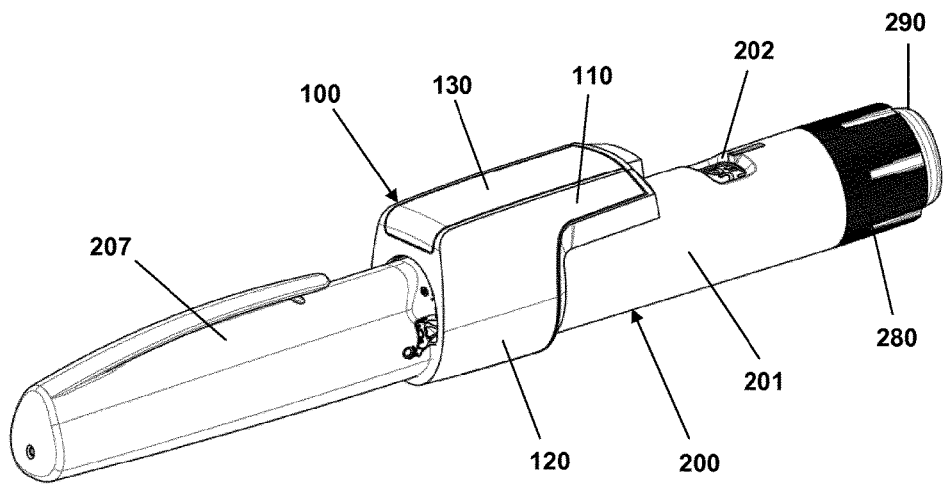
FIGS. 1A and 1B show a pen-formed drug delivery device with an electronic logging module.
Figure 1B:
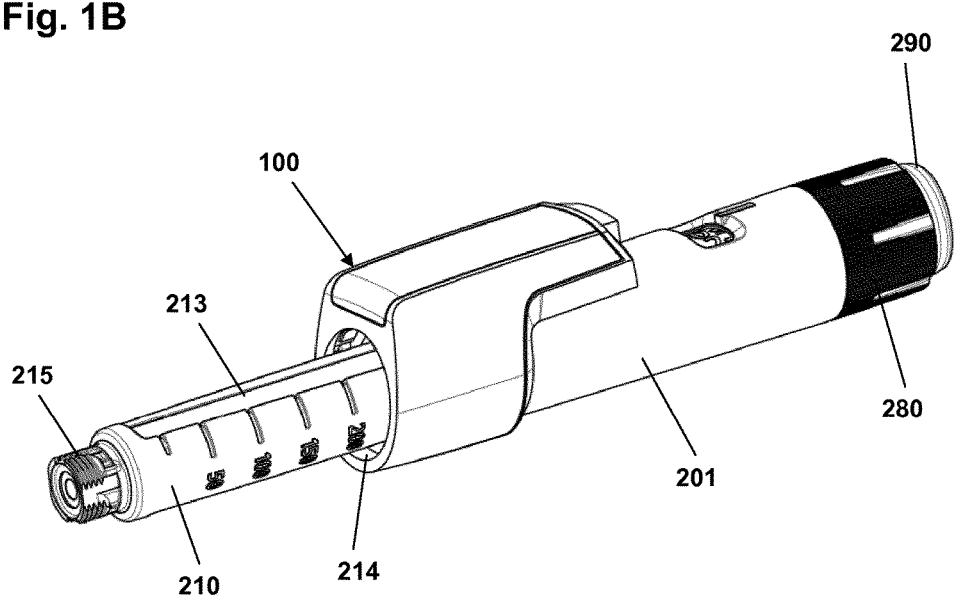

FIGS. 1A and 1B show a pen-formed drug delivery device 200 on which an electronic logging module 100 is mounted. In the present context the device represents a "generic" drug delivery device providing a specific example of a device in combination with which embodiments of the present invention is intended to be used or which can form a basis for aspects of the present invention.

More specifically, the logging module 100 comprises a body portion 110 and a ring-formed portion 120 allowing the module to be mounted on a generally cylindrical pen device. The body portion comprises electronic circuitry and sensor means allowing a property to be detected representing an amount of drug being expelled from the cartridge, as well as a display 130 for displaying data to a user. The ring portion comprises coupling means allowing the module to be securely and correctly mounted on the pen body. The electronic circuitry and the sensor means may in part be arranged in the ring portion. Depending on the sensor means provided in the logging module and the property to be detected, the drug delivery device may have to be adapted specifically to allow the given property to be detected. For example, the drug delivery device may be provided with a magnet rotating during dose expelling, the logging module being adapted to detect the amount of rotation, see below.

The pen device 200 comprises a cap part 207 and a main part having a proximal body or drive assembly portion with a housing 201 in which a drug expelling mechanism is arranged or integrated, and a distal cartridge holder portion in which a drug-filled transparent cartridge 213 with a distal needle-penetrable septum is arranged and retained in place by a non-removable cartridge holder attached to the proximal portion, the cartridge holder having openings allowing a portion of the cartridge to be inspected as well as distal coupling means 215 allowing a needle assembly to be releasably mounted. The cartridge is provided with a piston driven by a piston rod forming part of the expelling mechanism and may for example contain an insulin, GLP-1 or growth hormone formulation. A proximal-most rotatable dose member 280 serves to manually set (or dial) a desired dose of drug shown in display window 202 and which can then be expelled when the button 290 is actuated. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose.

FIGS. 1A and 1B show a drug delivery device of the pre-filled type, i.e. it is supplied with a pre-mounted cartridge and is to be discarded when the cartridge has been emptied. In alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removably attached to the main part of the device.

Figure 2:
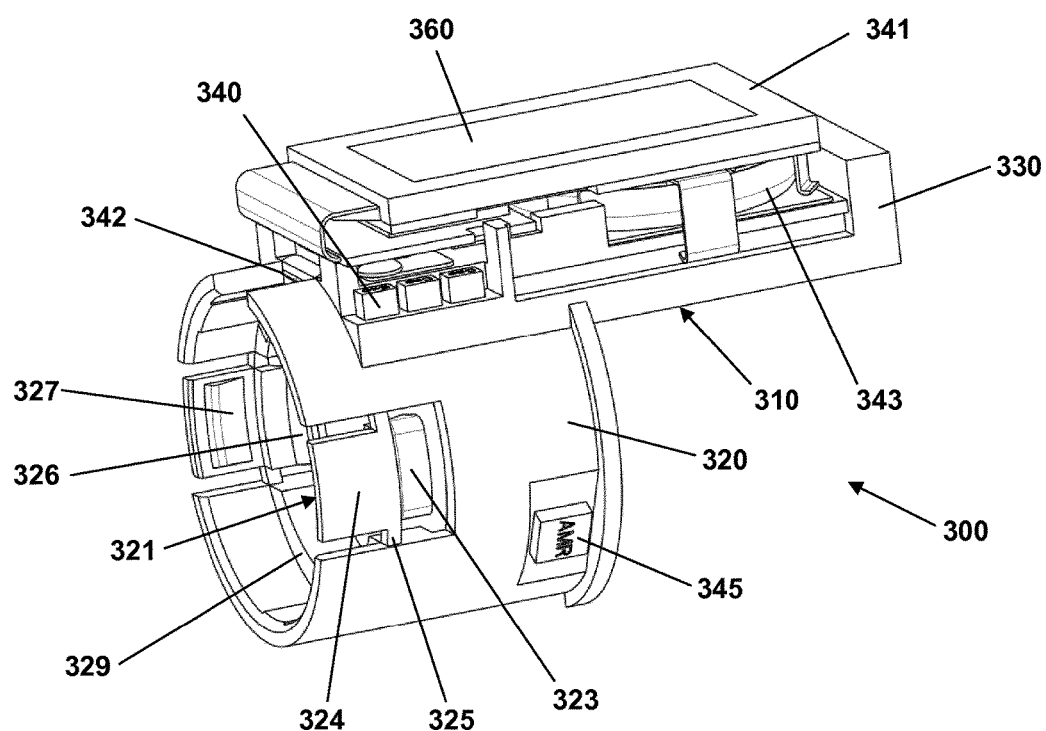
FIG. 2 shows the interior of a logging module.

Turning to FIG. 2 an exemplary embodiment of a logging module 300 is shown in which the exterior housing has been removed to reveal the interior design and components. The module comprises a main body 310 having a generally cylindrical ring-formed portion 320 and a body portion 330 together forming a chassis on which the majority of the electronic circuitry is mounted. The main body is formed from a LDS polymer whereby integrated wiring can be achieved by using LDS (Laser Direct Structuring) technology, the polymer having elastic properties allowing a flexible hinged latch to be formed integrally. Alternatively, the electronics including the sensors may be mounted on a flexible PCB which then is mounted on the main body 310 using e.g. metal clips. As a further alternative a flexible PCB may be mounted by fully or partly bonding it to a chassis component using double-sided adhesive, this allowing an accurate, reliable and compact design. The ring portion comprises an inner generally cylindrical surface adapted to be mounted on a drug delivery pen body as well as a pair of opposed integrally formed coupling structures 321 adapted to engage corresponding coupling structures on the pen device to assure that the module is securely mounted. The distal part of the ring portion has a larger diameter with a distally facing circumferential stop surface 329 adapted to receive and engage a cap when the module is mounted on a pen, see below.

The inner ring surface and the outer pen body surface may be in either form-fitting or slight frictional engagement. Each coupling structure on the module is in the form of a latch having a proximal portion 323, a distal portion 324 and a central portion, the latter being pivotally connected to the ring portion by integrally formed flexible hinges 325 allowing the latch to pivot a few degrees corresponding to a circumferential axis. By this arrangement the distal latch portion moves inwards when the proximal portion is moved outwards and vice versa. The proximal latch portions each comprises an inner protrusion 326 adapted to engage a corresponding coupling structure on the pen device (e.g. protrusions otherwise used for attachment of the cap) and the distal latch portions each comprises a protrusion 327 adapted to frictionally engage the cap outer surface when a cap is mounted after use. Alternatively the cap outer surface may be provided with coupling means, e.g. a circumferential groove, allowing the cap to engage the logging module by snap action. As appears for the shown embodiment, when the logging module is mounted on the drug delivery pen body, the cap attaches to the logging module and not the pen body. In alternative embodiments, the logging module may allow the cap to be attached directly to the pen body. To assure correct rotational mounting of the module on the pen the shown module is provided with a funnel-shaped slot adapted to axially engage a corresponding protrusion on the pen. In the shown embodiment of FIG. 1A a protrusion is provided on the pen cartridge holder 210 and arranged opposite the pen display window 202, the electronic display 130 thereby being arranged next to the pen display window when the module is mounted on a pen. The interactions between the logging module, the pen body and the cap will be described in greater detail below.

On the body portion 330 the majority of the electronic components 340 including processors means with associated memory means, a display module 341 with a display 360, a cap switch 342 for detecting the presence of a mounted cap, a main switch (not shown) for detecting that the logging module is mounted on a pen body, and an energy source 343 are mounted. The latter may be in the form of a non-replaceable device life-time "battery", a replaceable battery or in the form of a rechargeable battery. In the shown embodiment the LCD is of a traditional stiff type to be covered by a separate display window, however, alternatively a flexible LCD may be bonded directly to a transparent plastic cover providing a compact and robust design. In addition to the LCD a sound generator, e.g. a piezo beeper, may be provided to signal different states and/or error conditions to the user.

In the shown embodiment the logging module is provided with a first sensor assembly comprising three "compass" sensor units 345 mounted equidistantly on the ring portion 320, each sensor unit being in the form of a magnetometer adapted to measure a magnetic field corresponding to three axes. Another type and number of sensors arranged in another pattern may be used. In the shown embodiment the sensor system is designed to detect the amount of rotation of a magnetic member arranged inside the drug delivery device for which the logging module has been specifically designed, such a system being described in greater detail in PCT application EP 2014/056724 which is hereby incorporated by reference.

Further sensors may be provided allowing e.g. the type of the device (and thereby the drug) to be recognized, this being relevant if e.g. the drug delivery device is sold with a given drug in different concentrations such as insulin with 100 or 200 IU per ml. Alternatively, the logging module and the drug delivery device may be provided with mechanical coding means allowing a given logging module to be mounted only on a drug delivery device specifically coded for use with that logging module.

In the shown embodiment the logging module comprises a ring-formed portion providing a bore adapted to receive a drug delivery device. Alternatively the ring may be open and provided with a releasable closure member as disclosed in e.g. WO 2010/037828.

The logging module may be provided with user input means in the form of e.g. one or more buttons (not shown) allowing the user to control the module. The logging module may further be provided with transmission means allowing data to be transmitted to or from the module, e.g. log data may be transmitted to a user's smartphone by NFC or other wireless means.

Figure 3:
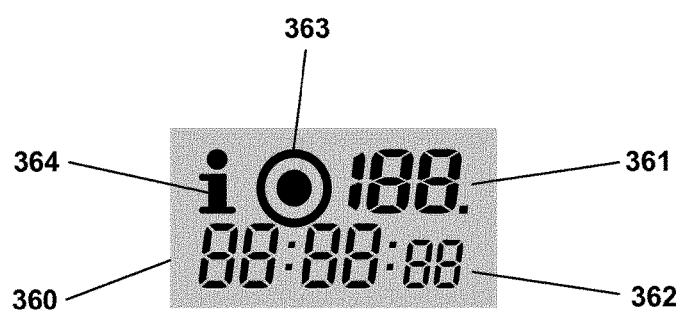
FIG. 3 shows a display with all segments active.

FIG. 3 shows an exemplary embodiment of a display 360 with all segments turned on. More specifically, the display comprises a dose size field 361 for showing a dose size in IU, a time field 362 having a stopwatch format HH:MM:SS, a "ready" symbol 363, and an "information" symbol 364. Exemplary use of the different display segments will be given below with reference to FIG. 4.

Figure 4:
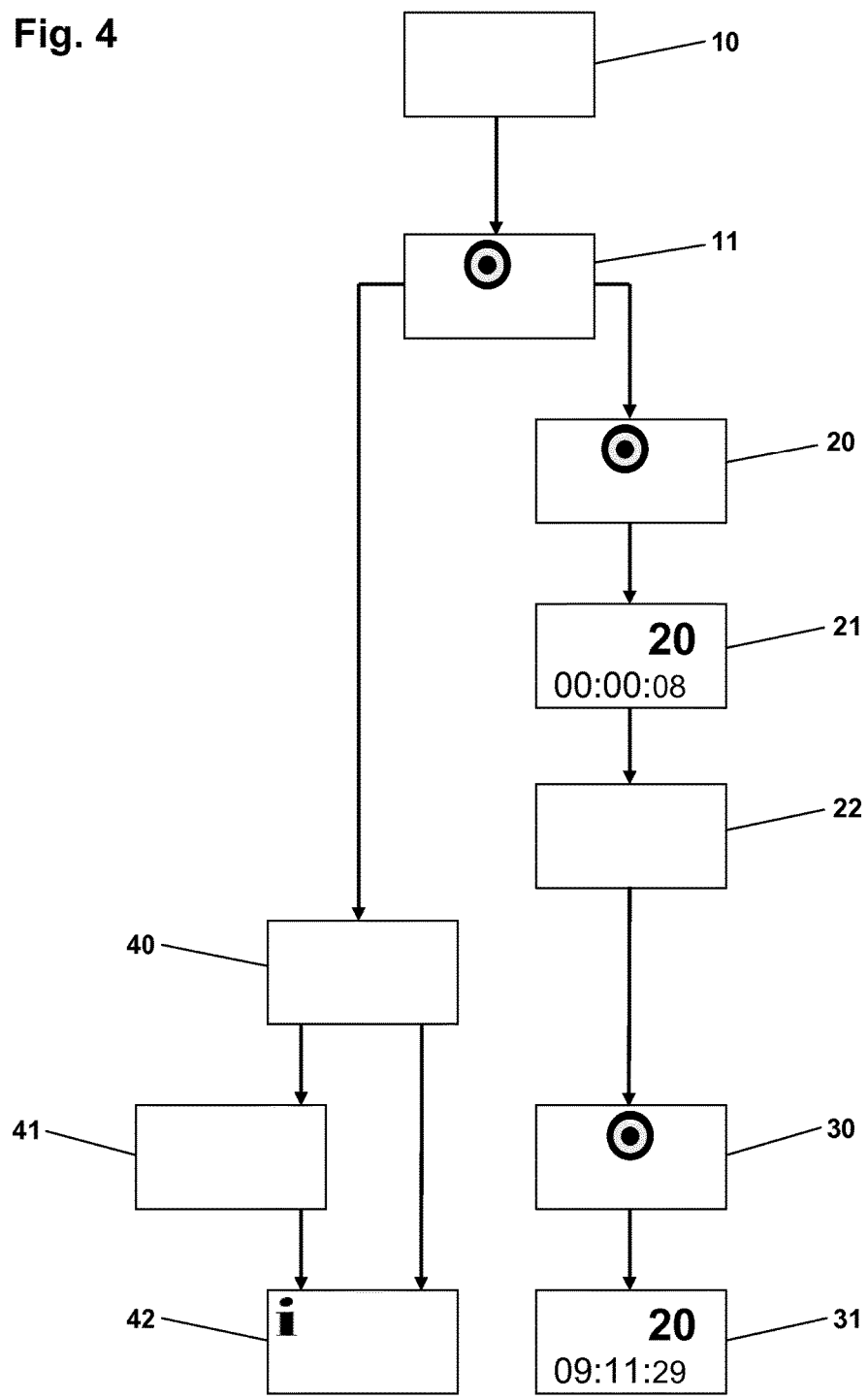
FIG. 4 shows a flowchart with display readings during different operational states.

Turning to FIG. 4 a flow-chart is shown in which different aspects of the logging module user interface is illustrated, i.e. how the different features of the logging module is used to provide a logging module which in combination with a corresponding drug delivery device, e.g. as shown in FIGS. 1A and 1B, is both easy to use and energy efficient, the latter being a requirement especially in case the logging module is provided with a non-exchangeable energy source intended to power the module for its intended life-time, e.g. three years of normal use for the average user.

When the mounted logging module is in its sleeping state the display 10 is blank with no segments active. When the user removes the cap, thereby activating the cap switch, the display 11 shows the "ready" symbol indicating that the sensor system is now turned on and the logging module is ready to detect and store a dose to be expelled. During dose setting and subsequent dose expelling the display 20 does not change but merely shows the ready symbol. When the user after having expelled a dose again attaches the cap the display 21 shows the expelled dose size in the dose size field, e.g. 20 IU as shown, together with a time value in the time field, e.g. 8 seconds as shown. As the latter has a stopwatch configuration with a running second counter it is apparent to the user that a "time-since-last-dose" is shown. At the same time the ready symbol is turned off. After a given number of seconds, e.g. 20 seconds, the display 22 is turned off. If the user later desires to check the latest log entry, i.e. dose size and time-since-last-dose, he or she activates the cap switch by moving the cap out of its mounted position thereby turning on the ready symbol in the display 30 and moves it back to its mounted position, the display 31 showing the last detected dose size together with the actual time-since-last-dose, e.g. 20 IU expelled 9 hours, 11 minutes and 29 seconds ago. To save energy the sensor system may be turned on with a delay of e.g. a few seconds, this allowing the user to check the latest log entry without the sensor system being turned on.

To safe-guard low energy consumption the sensor system will time out and turn off after a certain amount of time, e.g. 5 minutes, after which the ready symbol in the display 40 is turned off. The logging module may be designed to re-start the timer for each successful detection of an expelled dose, this allowing the user time to split a given dose into two or more doses. Although the blank display indicates to the user that the sensor system has been turned off, the drug delivery device can be used as usual to set and expel a desired dose, however, the sensor system will remain turned off and the display 41 will remain blank. However, in order to remind the user that any dose that may have been expelled during a time-out period has not been logged, the display 42 will turn on the information "i" symbol. As appears, whether or not a dose has been expelled, the user is presented with the "i" symbol when the cap is mounted again after a sensor time-out event. If the logging module is provided with an audible alarm, e.g. a beeper, the alarm may be sounded as well. In case the time-out appears after a successful detection of an expelled dose, the "i" will still be shown when the cap is put on, however, the detected dose has been stored and can be recalled as described below. Alternatively the "i" symbol may be replaced with a symbol more directly indicating an error condition.

With reference to FIG. 3 two exemplary logging module features have been described, i.e. (i) display showings during normal use, and (ii) display showing after a sensor time-out event.

Each of the two features may be implemented alone or in combination for a given logging module.

In addition to the above-described use scenarios, the display symbols and number fields can be used in additional ways. For example, the "i" symbol may be used in combination with a value shown in the dose size field to generate a number of codes, e.g. to indicate an error during dose sensing, a low battery condition or information in respect of data transfer, see below. Further, if the logging module is adapted to combine split doses (see EP 2014/056727) the "i" may be used to indicate that doses have been combined.

Figure 5:
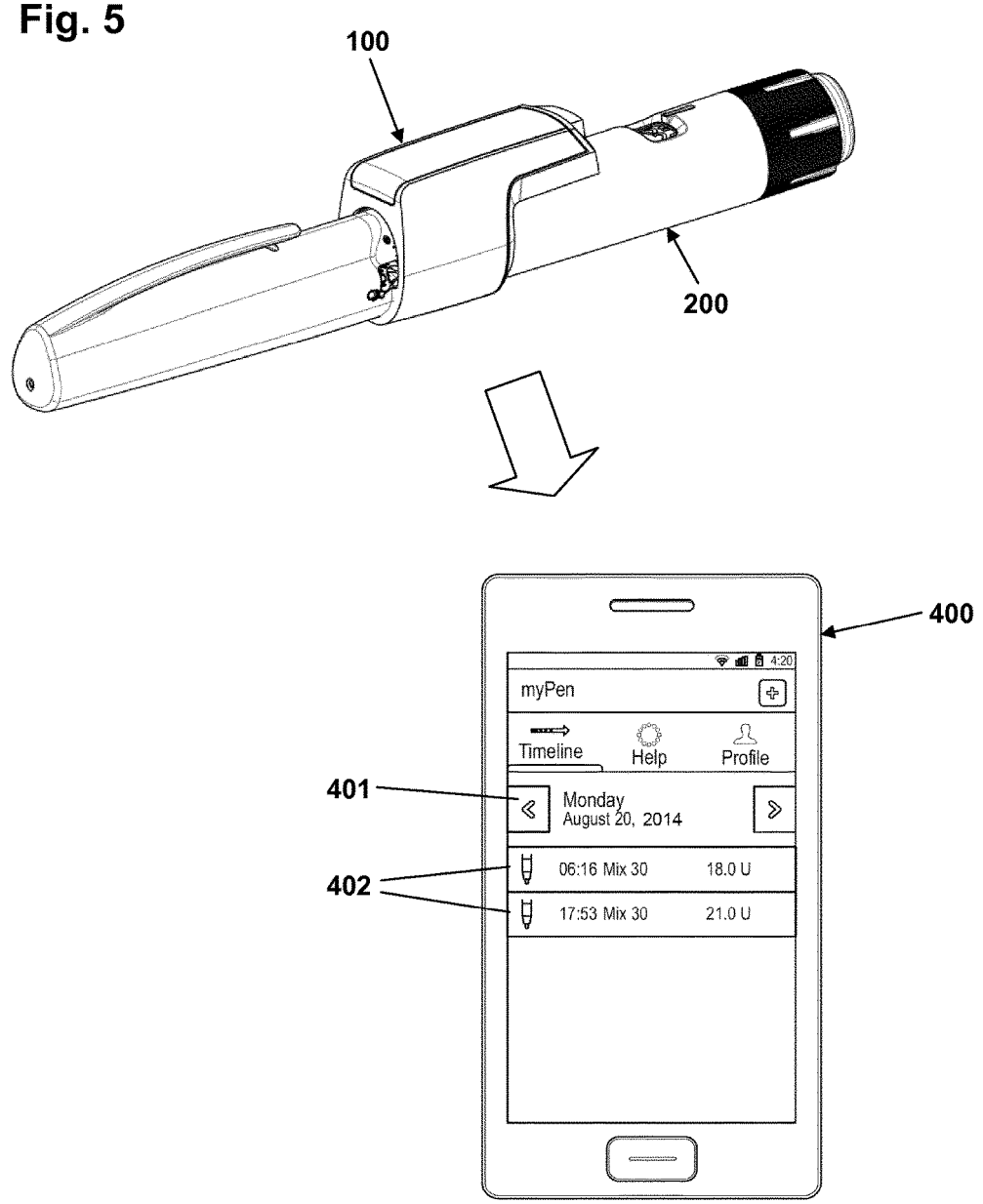
FIG. 5 shows a drug delivery pen provided with a logging module and in communication with a smartphone.

FIG. 5 shows a drug delivery pen 200 provided with a logging module 100 of the type described above with reference to FIGS. 1-4 and arranged next to a smartphone 400 configured to receive logging data from the logging module via wireless communication, e.g. NFC. As described above, the logging module is provided with a display configured to indicate the size of the last dose and the time since the last dose using the stopwatch display mode.

In order to communicate with the logging module the smartphone has been provided with specific "insulin diary" software. When the software is activated to initiate data transfer the smartphone NFC transmitter will transmit specific code which will wake up any nearby logging module which will then retransmit a unique code identifying the specific module. If a specific code is received for the first time the user is asked to confirm pairing and is asked to select from a list the given drug that should be associated with the given logging module, e.g. "Mix 30" as shown. Alternatively, the logging module may be designed to work with only one type of pen containing only one specific type of drug, the type of drug being transmitted during initial pairing, or the logging module may be provided with the ability to identify different types of pens and thus different types of drugs. In the shown embodiment log data from a logging module associated with a Mix 30 insulin has been transferred. Transfer may be controlled entirely by the smartphone, the logging module merely transmitting data when requested to do so. For example, when controlled to transfer logging data the logging module may transmit the entire memory content each time, e.g. 30 logging events, the smartphone being adapted to identify new log entries since last transfer. The stored logging data may comprise all determined dose amounts, i.e. including air shots and dose amounts determined in a sensor time-out event but before the sensors were turned off.

When data has been successfully transmitted this may be indicated on the smartphone as well as on the logging module. In the exemplary user interface the user can toggle back and forth between different day views, each day view showing the different amounts of drug delivered together with a real time value. In FIG. 5 on a given day 401 first and second amounts 402 of Mix 30 has been delivered with the time and amount shown for each delivery. It may be indicated if a given dose amount is based on combined dose amounts. To avoid having a real time clock in the logging module time information for each log entry may be generated by the smartphone based on relative time information provided by the logging module.

With reference to FIGS. 1-5 an electronic logging module adapted to be mounted on a performed drug delivery device has been described, however, the components of the module may alternatively be incorporated in a drug delivery device forming a unitary device. As such a device will comprise only a single housing the over-all volume may be reduced.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A logging device releasably attached to a drug delivery device, the drug delivery device comprising a drug reservoir or a structure for receiving the drug reservoir, the drug reservoir comprising an outlet portion, a detachable cap adapted to cover the drug reservoir outlet portion in a mounted position, and a drug expeller comprising a dose setter allowing a user to set a dose amount of a drug to be expelled, the logging device comprising:
electronic circuitry comprising:
a sensor adapted to capture a property value related to the dose amount of the drug expelled from the drug reservoir by the drug expeller during an expelling event when the logging device has been attached to the drug delivery device,
a processor adapted to determine dose amounts based on the captured property values,
a memory adapted to store at least one dose amount,
a display adapted to display a determined dose amount and/or a time value, and a warning message, and
a switch adapted to be operated by the detachable cap, when the logging device has been attached to the drug delivery device, between an off-state when the detachable cap is in the mounted position and an on-state when the detachable cap has been detached,
wherein:
the sensor is turned on when the switch is operated from the off-state to the on-state when the detachable cap is removed,
the sensor is turned off when the switch is operated from the on-state to the off-state when the detachable cap is remounted,
the sensor is turned off automatically when a predetermined amount of time has lapsed, and
the display is turned on to display the warning message when the switch is operated from the on-state to the off-state and when the sensor has been turned off automatically, the warning message indicating to the user that the expelled dose may not have been captured.

2. The logging device as in claim 1, wherein:
the display is turned on for a predetermined amount of time to display a message when the switch is operated from the on-state to the off-state, the message being in the form of:
a last determined dose amount and/or a time value when the display is turned on without the sensor having been turned off automatically, or
the warning message when the display is turned on with the sensor being turned off automatically.

3. The logging device as in claim 1, wherein stored dose amounts determined within a given time period are combined to a single combined dose amount, and the given time period is initiated by a detected expelling event taking place:
a given amount of time after a previously detected expelling event, or
after a given detected action.

4. The logging device as in claim 3, wherein two or more dose amounts determined within the given time period are combined automatically.

5. The logging device as in claim 3, wherein the user is prompted to accept that two or more dose amounts determined within the given time period are combined.

6. The logging device as in claim 3, wherein a determined dose amount below a given value is estimated to be a priming or air shot and is not combined with another log entry.

7. The logging device as in claim 1, wherein a log comprises a time value associated with each stored dose amount.

8. The logging device as in claim 1, wherein the sensor is adapted to capture the property value in the form of an amount of rotation of a magnetic member arranged in the drug delivery device, the amount of rotation of the magnetic member corresponding to the dose amount of the drug expelled from the drug reservoir by the drug expeller.

9. The logging device as in claim 1, wherein the sensor is turned on with a time delay when the switch is operated from the off-state to the on-state.

10. A drug delivery system, comprising:
a drug reservoir or a structure for receiving the drug reservoir, the drug reservoir comprising an outlet portion;
a detachable cap adapted to cover the drug reservoir outlet portion in a mounted position;
a drug expeller comprising a dose setter allowing a user to set a dose amount of a drug to be expelled; and
electronic circuitry comprising:
a sensor adapted to capture a property value related to the dose amount of the drug expelled from the drug reservoir by the drug expeller during an expelling event,
a processor adapted to determine dose amounts based on the captured property values,
a memory adapted to store at least one dose amount,
a display adapted to display a determined dose amount and/or a time value, and a warning message, and
a switch operable by the detachable cap between an off-state when the detachable cap is in the mounted position and an on-state when the detachable cap has been detached from the drug delivery system,
wherein:
the sensor is turned on when the switch is operated from the off-state to the on-state when the detachable cap is removed,
the sensor is turned off when the switch is operated from the on-state to the off-state, the sensor is turned off automatically when a predetermined amount of time has lapsed, and the display is turned on to display the warning message when the switch is operated from the on-state to the off-state and when the sensor has been turned off automatically, the warning message indicating to the user that the expelled dose may not have been captured.

11. The drug delivery system as in claim 10, wherein the system is in the form of a drug delivery device comprising:
the drug reservoir,
the drug expeller, and
the electronic circuitry.

12. The drug delivery system as in claim 10, wherein the sensor is adapted to capture the property value in the form of an amount of rotation of a magnetic member arranged in the drug delivery device, the amount of rotation of the magnetic member corresponding to the dose amount of the drug expelled from the drug reservoir by the drug expeller.

13. The drug delivery system as in claim 10, wherein two or more dose amounts determined within a given time period are combined automatically.

14. The drug delivery system as in claim 10, the drug delivery device further comprising:
an identifier representing information for a specific drug type contained in the drug reservoir or a specific drug delivery device, and
a logging device for capturing information from the identifier,
wherein the electronic circuitry is adapted to create a log for a given identifier.

\* \* \* \* \*